United States Patent [19]

Kaelin

[11] 4,244,131
[45] Jan. 13, 1981

[54] AIMING DEVICE FOR A FIREARM

[75] Inventor: Joseph R. Kaelin, Buochs, Switzerland

[73] Assignee: Escope Trading Company Aktiengesellschaft, Zug, Switzerland

[21] Appl. No.: 6,964

[22] Filed: Jan. 25, 1979

[30] Foreign Application Priority Data

Feb. 1, 1978 [CH] Switzerland ............... 1122781/78

[51] Int. Cl.³ .......................................... F41F 3/00
[52] U.S. Cl. ..................................................... 42/1 A
[58] Field of Search ......................................... 42/1 A

[56] References Cited

U.S. PATENT DOCUMENTS

| 3,867,764 | 2/1975 | Dunmire et al. | 42/1 A |
| 4,026,054 | 5/1977 | Snyder | 42/1 A |
| 4,069,414 | 1/1978 | Bell | 42/1 A |
| 4,079,534 | 3/1978 | Snyder | 42/1 A |
| 4,152,754 | 5/1979 | de Filippis et al. | 42/1 A |
| 4,161,076 | 7/1979 | Snyder | 42/1 A |

FOREIGN PATENT DOCUMENTS 1286707  1/1962  France ........................... 42/1 A Primary Examiner—Charles T. Jordan
Attorney, Agent, or Firm—Ladas & Parry

[57] ABSTRACT

An aiming device for a firearm comprising a laying device adapted to be fitted on the firearm parallel thereto, a laser device and a power supply. The laying device has a double articulation on which the front part of the laser device is mounted, and an adjusting facility having an articulation and a vertical rod, the bottom part of the laser device being retained on the facility for movement in two directions, so that vertical and lateral drift can be adjusted for by means of two adjusting mechanisms.

The power supply comprising at least one battery is for energising the laser device and is disposed therein or outside it.

5 Claims, 4 Drawing Figures

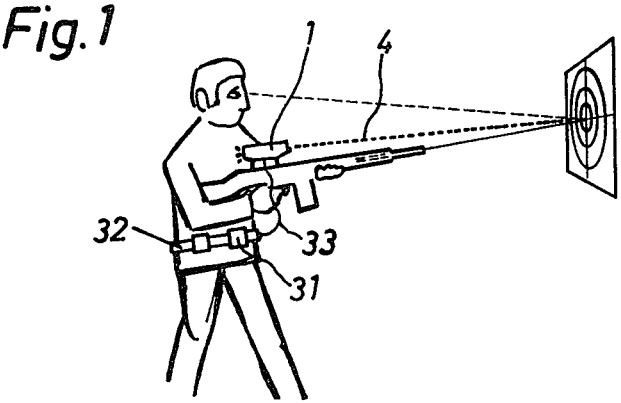
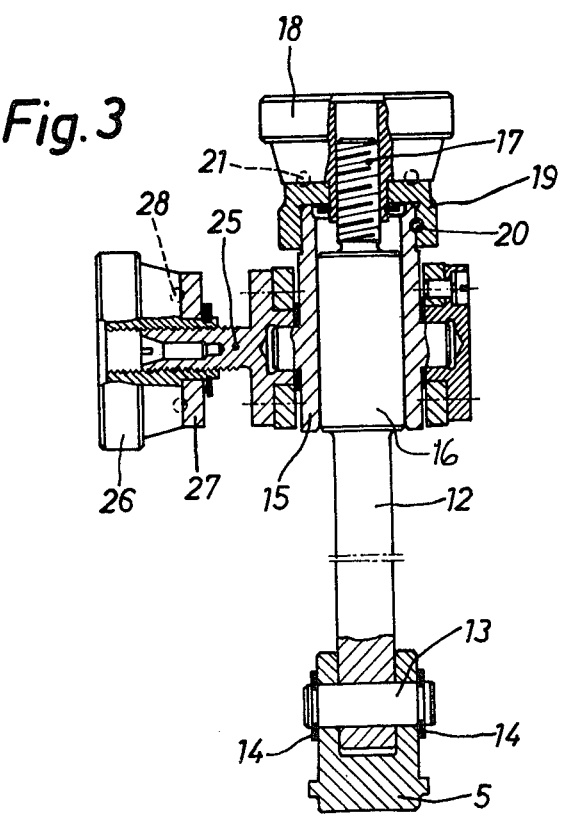

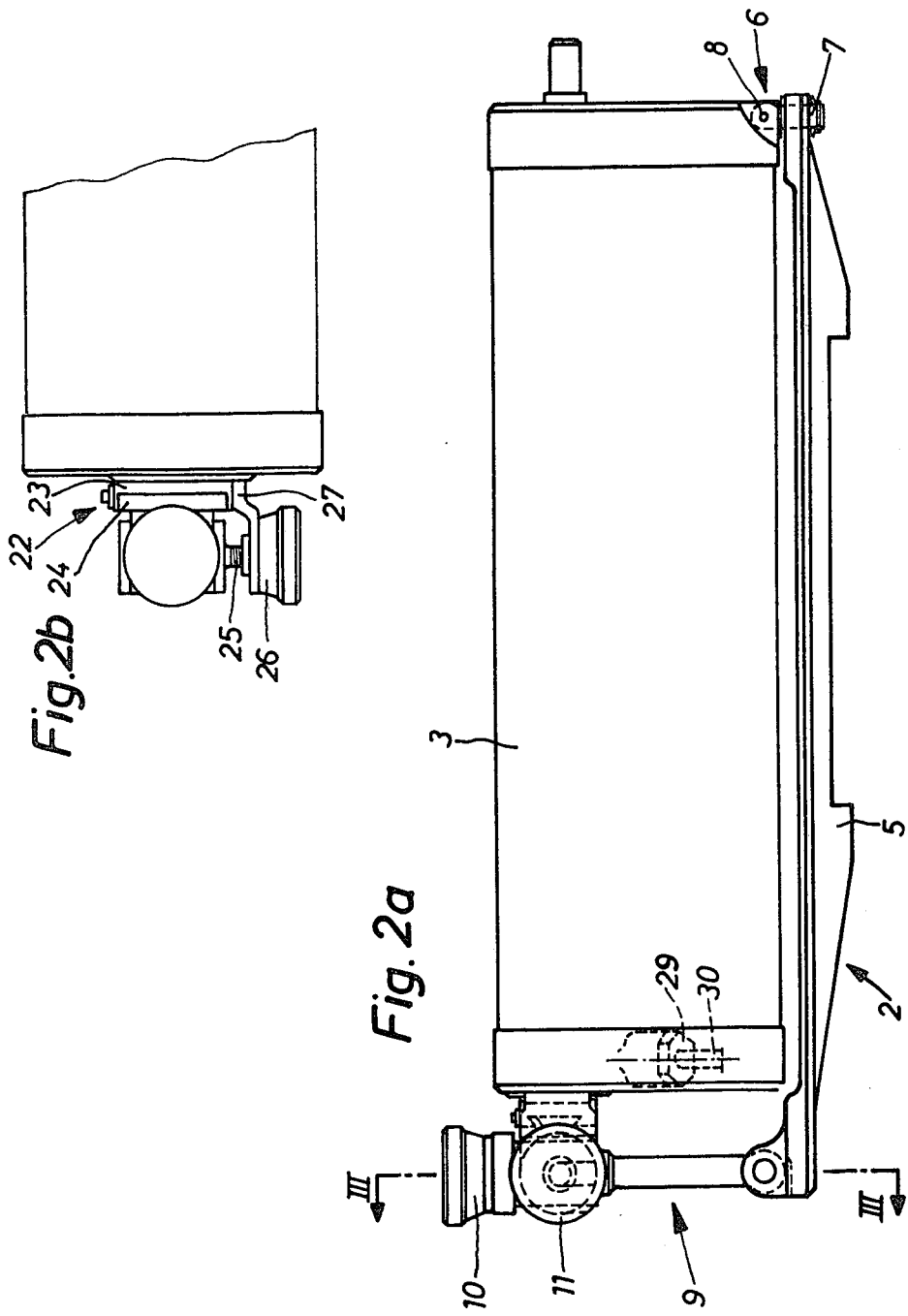

AIMING DEVICE FOR A FIREARM

DESCRIPTION

The invention relates to an aiming device for a firearm and comprises a laying device adapted to be fitted on the firearm parallel thereto, a laser device disposed on the laying device and emitting beams in the direction of the firearm muzzle and a power supply for energising the laser device.

Optical aiming devices and facilities are known e.g. from Swiss Patent Specification Nos. 508,190 and 538,666.

In another known kind of aiming device laser beams are used to give clearer visualisation of a target.

The disadvantage of such devices is that different targets at different distances cannot be hit.

It is an object of the invention to obviate this disadvantage.

It is therefore an object of the invention to provide an aiming device which can be fired accurately even from the hip and can be rapidly adjusted in combat for necessary distance and side drift corrections.

This problem is solved by the aiming device according to the invention wherein the laying device comprises a bottom part and an adjusting facility for adjusting for the vertical and lateral drift of a projectile, the laser device being pivotally mounted at its front end on the bottom part and being retained at its rear end on the adjusting facility for movement in two directions.

Conveniently, a double articulation having two pivot axes perpendicular to one another is provided so that the laser device is pivotable around an axis which is vertical in relation to the bottom part and laterally around an axis extending horizontally of the bottom part, and the adjusting facility comprises a first adjusting mechanism pivotally mounted on the bottom part and a second adjusting mechanism which is retained on the laser device and on the first adjusting mechanism, the laser device being adjusted for height by the first adjusting mechanism and laterally by the second adjusting mechanism, in both cases in relation to the bottom part.

In an embodiment of the invention, the power supply comprises at least one battery which can be connected to the laser device by way of an electric cable and a plug-in device.

The weight of the aiming device and the handling of the firearm are therefore reduced in an advantageous manner. Also, a relatively high-performance battery can be used, so that the radiation power of the laser device can be increased and the distance to the target can be increased.

An embodiment of the invention will be described now by way of example only with particular reference to the accompanying drawings wherein:

FIG. 1 is a view showing the use of an embodiment of an aiming device according to the invention;

FIGS. 2a and 2b are a side view and plan view respectively of the aiming device, and FIG. 3 is a section on the line III—III of FIG. 2a.

FIG. 1 shows a person aiming a submachine gun held on the hip at a target. The submachine gun has an aiming device 1 according to the invention which is fitted on the submachine gun parallel thereto.

FIGS. 2a and 2b show an embodiment of the aiming device. The aiming device 1 mainly comprises a laying device 2 and a laser device 3. The laser device 3, in response to operation by an element which is not shown, emits a laser beam 4 which, as FIG. 1 shows, is directed towards the target so that the hit is indicated to the marksman by a scintillating spot on the target.

The laser device is a known construction and so will not be described in detail.

The laying device 2 comprises a bottom part 5 formed with a recess. As FIG. 1 shows, the aiming device 1 is so fitted to the submachine gun that the laser device 3 emits beams in the direction of the firearm muzzle. The bottom part 5 is secured to the gun by appropriate means, such as screws (not shown).

Disposed at that end of the bottom part 5 which is at the front in relation to the gun is a double articulation 6 comprising two pivot axes perpendicular to one another. Articulation 6 has a pivot pin 7, one part of which is secured in the bottom part 5 for pivoting around an axis perpendicular to the part 5. The other part of pin 7 projects from the top of the bottom part 5 and is bifurcated. The front part of the laser device 3 is mounted by way of a shaft 8 in the fork for pivoting around an axis extending horizontally in relation to the bottom part 5.

An adjusting facility 9 is provided at that end of the bottom part 5 which is at the rear in relation to the gun. The facility 9 has a first adjusting mechanism 10, which is connected to the bottom part 5, and a second adjusting mechanism 11, which is connected to the first adjusting mechanism 10 and to the laser device 3.

FIG. 3 is a view of the adjusting facility 9 in section.

The mechanism 10 for vertical adjustment has a pin 12 pivotally mounted at one end on the bottom part 5 by way of a pivot pin 13 secured by circlips 14 in a bifurcated mounting. A sleeve or collar or the like 15 is adapted to move on an increased diameter portion 16 of pin 12.

At its other end the pin 12 has a screwthreaded portion 17 on which an adjusting wheel 18 is screwed. Between the wheel 18 and the sleeve 15 there is a catch ring 19, the same has a tubular extension which is placed on the sleeve 15 and secured by two pins 20. Between the wheel 18 and the ring 19 there are a number of balls 21 which are disposed in the wheel 18 and which are engageable in recesses (not shown) in the ring 19. The catch resistance can be adjusted by providing from one to four balls.

The mechanism 11 for horizontal adjustment is connected to the sleeve 15 and to the laser device 3. To facilitate movement of the laser device 3 a dovetail guide 22 is provided whose bed 23 is screwed to the laser device 3 and whose slide 24 is secured to the sleeve 15. Disposed thereon is a screwthreaded pin 25 which projects from the sleeve 15 parallel to guide 22. Another adjusting wheel 26 is screwed on to pin 25. Wheel 26 has a projection receiving a bent plate 27 secured by way of its bent end to the laser device 3. The plate 27 transmits to the laser device 3 the lateral movement initiated by the handwheel 26. Between the wheel 26 and that part of the plate which engages therewith are a number of balls 28 which are disposed in the wheel 26 and which are engageable in recesses (not shown) in that part of the plate 27 which is in engagement with wheel 26. As in the case of the vertical adjusting mechanism 10, the catch resistance can be adjusted.

Both the adjusting wheels 18, 26 have a scale.

A cable enters the rear of the laser device 3 through a grommet or the like 29 and serves to carry an electrical signal for starting the laser device 3 so that a laser beam is transmitted intermittently.

The operation of the adjusting facility 9 will be described hereinafter. When an aiming device has been fitted to the gun, the drift of a projectile can be corrected for by means of the adjusting facility 9, the wheels 18 and/or 26 being rotated clockwise or anticlockwise to make the adjustment, vertical drift being corrected for by wheel 18 and lateral drift by wheel 26. The wheels 18, 26 have scales to facilitate adjustment. Because of the ball catch mechanism, adjustment proceeds stepwise, thus ensuring reliable location of the setting to which the mechanism is adjusted.

The aiming device described can correct for a drift of 0.796° in each of the four adjustment positions—i.e., a maximum of 1.592° in each plane of adjustment.

As FIG. 1 shows, the power supply comprises a number of batteries 31 secured to a belt or strap 32. The batteries 31 are connected by an electric cable 33 to the laser device 3. To facilitate handling of the weapon, the cable 33 is connected to the laser device 3 by way of a plug-in device (not shown). The same can have a snap device for rapid connection.

The batteries 31 can be carried on a carrier (not shown) worn over the shoulder.

Another possibility is for the batteries to be in a bullet-proof jacket.

The use of separate batteries greatly facilitates battery replacement, which can be carried out by unskilled operators since the laser device 3 itself does not have to be opened.

I claim:

1. An aiming device for a firearm comprising:

a laying device adapted to be fitted on the firearm parallel thereto and comprising a bottom part and an adjusting facility for adjusting the laying device to compensate for vertical and lateral drift of a projectile;

a laser device which is disposed on the laying device and is arranged to emit beams in the direction of the firearm muzzle, the laser device being pivotally mounted at its front end on the bottom part of the laying device and being retained at its rear end on the adjusting facility for movement in two directions, said adjusting facility comprising a first adjusting mechanism which is pivotally mounted on the bottom part and a second adjusting mechanism which is retained on the laser device and on the first adjusting mechanism, the laser device being adjustable for height by the first adjusting mechanism and laterally by the second adjusting mechanism, in both cases in relation to the bottom part; and means for supplying power for energizing the laser device.

2. An aiming device according to claim 1 wherein the first adjusting mechanism comprises a retaining element secured to one end of the bottom part, a sleeve disposed for movement on the other end of the retaining element and an adjusting wheel for moving the sleeve relatively to the retaining element and the second adjusting mechanism comprises a dovetail guide whose bed is secured to the laser device and whose slide is secured to the sleeve of the first adjusting mechanism and an adjusting wheel for moving the bed relatively to the slide.

3. An aiming device according to claim 2 wherein the adjusting wheels each have a catch device having at least one ball engageable by spring force with the adjusting wheel, and an adjusting scale.

4. An aiming device according to claim 3 characterised in that the catch device has four balls.

5. An aiming device according to claim 1 wherein the power supply comprises at least one battery which is connected to the laser device via an electric cable.

* * * * *